United States Patent
Dorvil

(10) Patent No.: US 9,865,183 B2
(45) Date of Patent: Jan. 9, 2018

(54) SYSTEM AND METHOD FOR CREATING SPACE FOR IDENTIFICATION LABELS ON MEDICATION DISPENSERS

(71) Applicant: Boryana Dorvil, Hamilton, NJ (US)

(72) Inventor: Boryana Dorvil, Hamilton, NJ (US)

(*) Notice: Subject to any disclaimer, the term of this patent is extended or adjusted under 35 U.S.C. 154(b) by 0 days.

(21) Appl. No.: 15/403,164

(22) Filed: Jan. 10, 2017

(65) Prior Publication Data

US 2017/0200402 A1   Jul. 13, 2017

Related U.S. Application Data

(60) Provisional application No. 62/277,090, filed on Jan. 11, 2016.

(51) Int. Cl.
*G09F 3/10* (2006.01)
*A61M 5/31* (2006.01)
*G09F 3/02* (2006.01)

(52) U.S. Cl.
CPC .......... *G09F 3/10* (2013.01); *A61M 5/31* (2013.01); *A61M 2005/3125* (2013.01); *A61M 2205/583* (2013.01); *G09F 2003/0272* (2013.01)

(58) Field of Classification Search
CPC .......... G09F 3/18; G09F 2003/0272; G09F 2003/0273; A61M 2005/3125; A61M 2205/583
See application file for complete search history.

(56) References Cited

U.S. PATENT DOCUMENTS

| | | | | |
|---|---|---|---|---|
| 1,353,531 A | * | 9/1920 | Heard | G09F 3/04 40/310 |
| 2,177,359 A | * | 10/1939 | Baker | B65D 23/065 215/386 |
| 2,194,220 A | | 3/1940 | Elder | |
| 2,250,666 A | * | 7/1941 | Godefroy | B65D 23/12 206/219 |
| 4,312,523 A | | 1/1982 | Haines | |
| 4,656,767 A | | 4/1987 | Tarrant | |
| 4,658,974 A | * | 4/1987 | Fujita | B65D 23/085 215/12.2 |
| 4,818,850 A | | 4/1989 | Gombrich et al. | |
| 4,857,713 A | | 8/1989 | Brown | |
| 4,921,277 A | | 5/1990 | McDonough | |
| 5,301,857 A | * | 4/1994 | Green | A45F 5/02 215/365 |
| 5,390,435 A | * | 2/1995 | Grody | G09F 23/06 40/310 |

(Continued)

*Primary Examiner* — Gary C Hoge
(74) *Attorney, Agent, or Firm* — LaMorte & Associates, P.C.

(57) ABSTRACT

A labeling system that enables labels to be attached to medication dispensing products that lack adequate surface area for the labels. The labeling system utilizes a panel having a first planar surface with a geometric center. The first planar surface extends to a periphery having a polygonal shape. An opening is formed in the panel proximate the geometric center. The opening is sized to receive the medication dispenser. Labels are adhered to the first planar surface. The polygonal shape of the panel provides its periphery with a first number of flat side surfaces. The polygonal shape is a visual indicator, wherein the labels adhered to the first planar surface correspond in number to the flat side surfaces along the periphery.

14 Claims, 6 Drawing Sheets

(56) References Cited

U.S. PATENT DOCUMENTS

| | | | | |
|---|---|---|---|---|
| 5,468,022 A | * | 11/1995 | Linder | G09F 3/205 283/72 |
| 5,555,655 A | * | 9/1996 | Yager | F17C 13/003 40/306 |
| 5,692,640 A | * | 12/1997 | Caulfield | G09F 3/10 221/199 |
| 5,826,356 A | * | 10/1998 | Lapp | B65D 5/4233 229/74 |
| 5,947,672 A | * | 9/1999 | Cohen | G09F 3/04 40/310 |
| 5,960,973 A | * | 10/1999 | Markson | G09F 3/04 215/386 |
| 5,984,901 A | * | 11/1999 | Sudo | A61M 5/3135 604/227 |
| 6,685,678 B2 | * | 2/2004 | Evans | G06F 19/3468 604/200 |
| 6,722,404 B2 | | 4/2004 | Osborne | |
| 6,957,522 B2 | | 10/2005 | Baldwin et al. | |
| 7,469,518 B2 | * | 12/2008 | Baldwin | A61M 5/28 53/250 |
| 7,774,962 B1 | * | 8/2010 | Ladd | G09F 3/0295 215/286 |
| D653,107 S | * | 1/2012 | Margan | D9/434 |
| D676,572 S | * | 2/2013 | Tarriff | D24/224 |
| 8,671,602 B2 | | 3/2014 | Seidl | |
| D701,762 S | * | 4/2014 | Gortot | D9/434 |
| 2005/0126950 A1 | | 6/2005 | Kaufman | |
| 2006/0240249 A1 | | 10/2006 | McCarthy et al. | |
| 2006/0283059 A1 | * | 12/2006 | Cope | G09F 3/04 40/310 |
| 2007/0138187 A1 | * | 6/2007 | Glass | B65D 23/14 220/694 |
| 2008/0188814 A1 | | 8/2008 | Lavi-Loebl et al. | |
| 2009/0291240 A1 | | 11/2009 | Moosheimer et al. | |
| 2010/0326866 A1 | | 12/2010 | Seidl | |
| 2011/0220713 A1 | | 9/2011 | Cloninger | |
| 2013/0239449 A1 | * | 9/2013 | Heinrichs | G09F 3/0288 40/665 |
| 2014/0352603 A1 | * | 12/2014 | Gortot | G09F 3/02 116/308 |
| 2016/0361529 A1 | * | 12/2016 | Finch, Jr. | A61M 39/0247 |

\* cited by examiner

SYSTEM AND METHOD FOR CREATING SPACE FOR IDENTIFICATION LABELS ON MEDICATION DISPENSERS

RELATED APPLICATIONS

This application claims the benefit of U.S. Provisional Patent Application No. 62/277,090, filed Jan. 11, 2016.

BACKGROUND OF THE INVENTION

1. Field of the Invention

In general, the present invention relates to auxiliary structures that attach to medication dispensers, such as insulin pens or inhalers. More particularly, the present invention relates to auxiliary structures that attach to medication dispensers for the purpose of providing additional room for identifying labels.

2. Prior Art Descriptions

Many hospitals track the administration of medications to patients using barcode labels. Often a different barcode label is created each time a patient is to receive a dose of medication in a given day. The barcode labels are then attached to the medication. The barcode is scanned when the dose of medication is given to the patient. In this manner, the computer system of the hospital can keep accurate records of what medications were given to what patients at what times. The tracking system also ensures that patients are receiving the proper medications and that cross-contamination is not occurring between patients through accidental occurrences of shared medications.

For pill medications, the barcode labels are commonly attached to the container that holds the pills. Otherwise, individual pills are packaged and labeled. In both cases, the pills are easily identified. A problem occurs when the patient's medication is provided in a multi-dose container, such as an insulin pen or an inhaler, wherein the same multi-dose container needs to be reused during the entire stay at the healthcare facility. In such a situation, multiple barcodes must be applied to the container each day. The labels include patient-specific unit-dose barcode labels. However, there is often not enough space on the products to place such labels. For example, a patient may be required to receive insulin four times a day. In order to use an insulin pen within a hospital's barcode tracking system, four barcode labels would have to be attached to the insulin pen each day. This is nearly an impossibility given the space available on the insulin pen.

Referring to FIG. 1, a typical prior art insulin pen 10 is shown. As can be seen, the insulin pen 10 has a first section 12 that is used to indicate injection dose. The insulin pen 10 has a second section 14 for altering the injection dose. Furthermore, the injection pen 10 has a third section 16 that provides necessary information about the insulin pen 10, including its contents, concentrations and expiration. In order to attach multiple barcode labels to this insulin pen, one or more of the pen's sections will be at least partially covered by a barcode label. As such, a healthcare worker may not be able to clearly view the three sections 12, 14, 16 of the insulin pen 10. This can lead to mistakes in dosage or lead to the administration of the wrong medication to the wrong patient.

Furthermore, if a label is attached to a medication dispenser, such as an insulin pen or an inhaler, the label typically must be contacted by the fingers of the person using the device. This can cause the information on the label to smear or fade. This also can lead to mistakes in dosage or lead to the administration of the wrong medication to the wrong patient.

In the prior art, some systems have been developed in an attempt to increase the areas that are available for the placement of a barcode label. In these prior art systems, flaps are attached to the syringe that extend away from the syringe and provide room for labels. However, the flaps attach to the syringe by covering much of the exterior of the syringe. In these prior art systems, the label attachment device covers just as much of the syringe as would the barcode labels themselves. Accordingly, this inhibits a person from identifying and properly utilizing the syringe. Such prior art systems are exemplified in U.S. Pat. No. 6,957,522 to Baldwin, entitled Method and System for Labeling Syringe Bodies, and U.S. Pat. No. 6,722,404 to Osborne, entitled Syringe Bandolier With Control Feature. Thus, the prior art systems do not address the problem of having sections of the syringe blocked from sight.

A need therefore exists for a system and method that can attach multiple labels to a small dispenser, such as a syringe or an inhaler, without blocking significant areas of the dispenser from view. The present invention attaches to medication dispensers in a hospital setting and provides extra space for multiple patient-specific unit-dose barcode labels. This enables patient specific multi-dose medication dispensers, such as insulin pens, to be used in place of vial administration systems. Multi-dose insulin pens have been proven to be superior to insulin vials and syringes not only in home use but in hospital use as well with respect to quality of care, patient safety, and cost. Unfortunately, they do not provide enough room for labeling and when used in hospital settings they can be easily misplaced or confused with another patient's insulin pen. Hospitals that use scanning systems for patient safety must scan the Rx barcode number. Unfortunately, this does not eliminate the possibility of cross contamination. The FDA recognized that danger long ago and has been trying to find a solution. The solution is provided by the present invention as described and claimed below.

SUMMARY OF THE INVENTION

The present invention is a labeling system that enables labels to be attached to medication dispensing products that lack adequate surface area for the labels.

The labeling system utilizes a panel having a first planar surface with a geometric center. The first planar surface extends to a periphery having a polygonal shape. An opening is formed in the panel proximate the geometric center. The opening is sized to receive the medication dispenser. Labels are adhered to the first planar surface. The polygonal shape of the panel provides its periphery with a first number of flat side surfaces. The polygonal shape is a visual indicator, wherein the labels adhered to the first planar surface correspond in number to the flat side surfaces along the periphery.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

The present invention system and method can be applied to many devices that hold and/or dispense medications. Accordingly, the present invention can be embodied in many ways to fit various devices. In the description provided below, only a few exemplary embodiments have been selected for the purposes of illustration and discussion. The exemplary embodiments illustrated and described present some of the best modes contemplated for the invention. The exemplary embodiments, however, are merely exemplary and should not be considered limitations when interpreting the scope of the appended claims.

Figure 1:
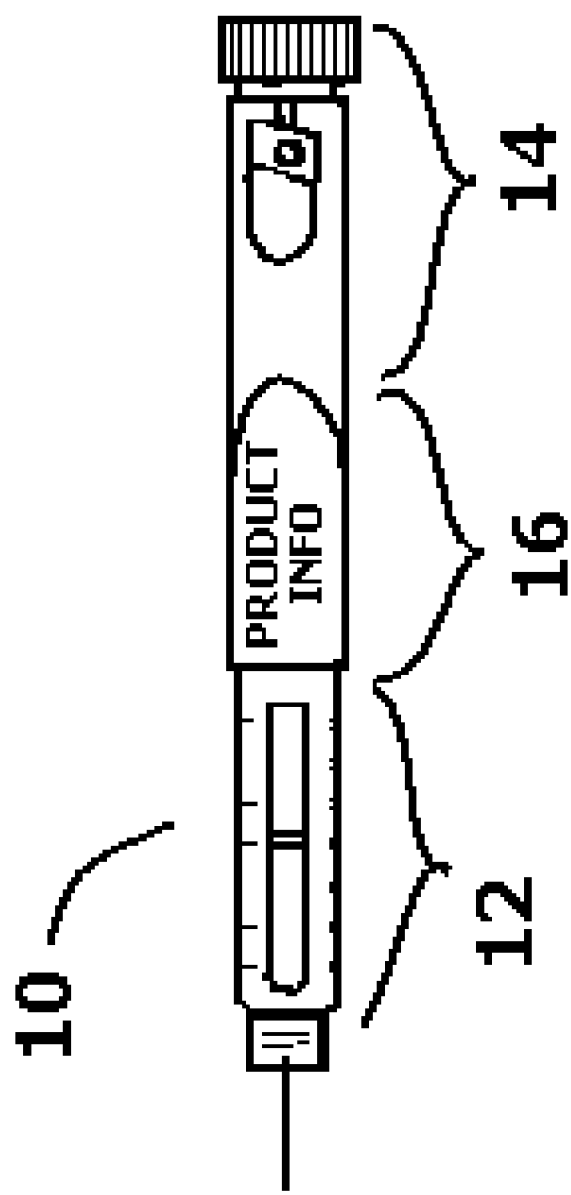
FIG. 1 is a prior art medication dispenser in the form of an insulin pen.
Figure 2:
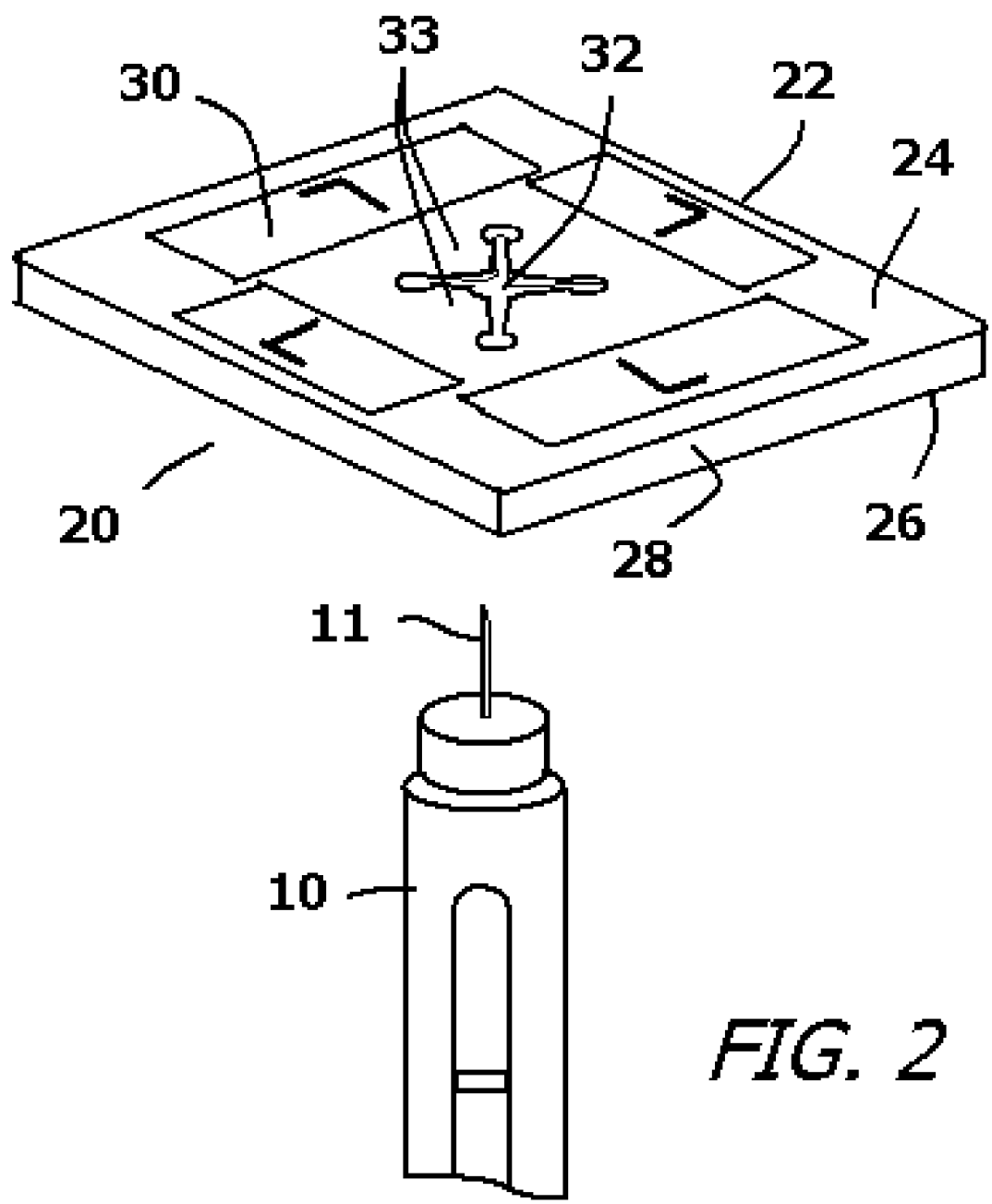
FIG. 2 shows the insulin pen of FIG. 1 in conjunction with an exemplary embodiment of the present invention labeling system.
Figure 3:
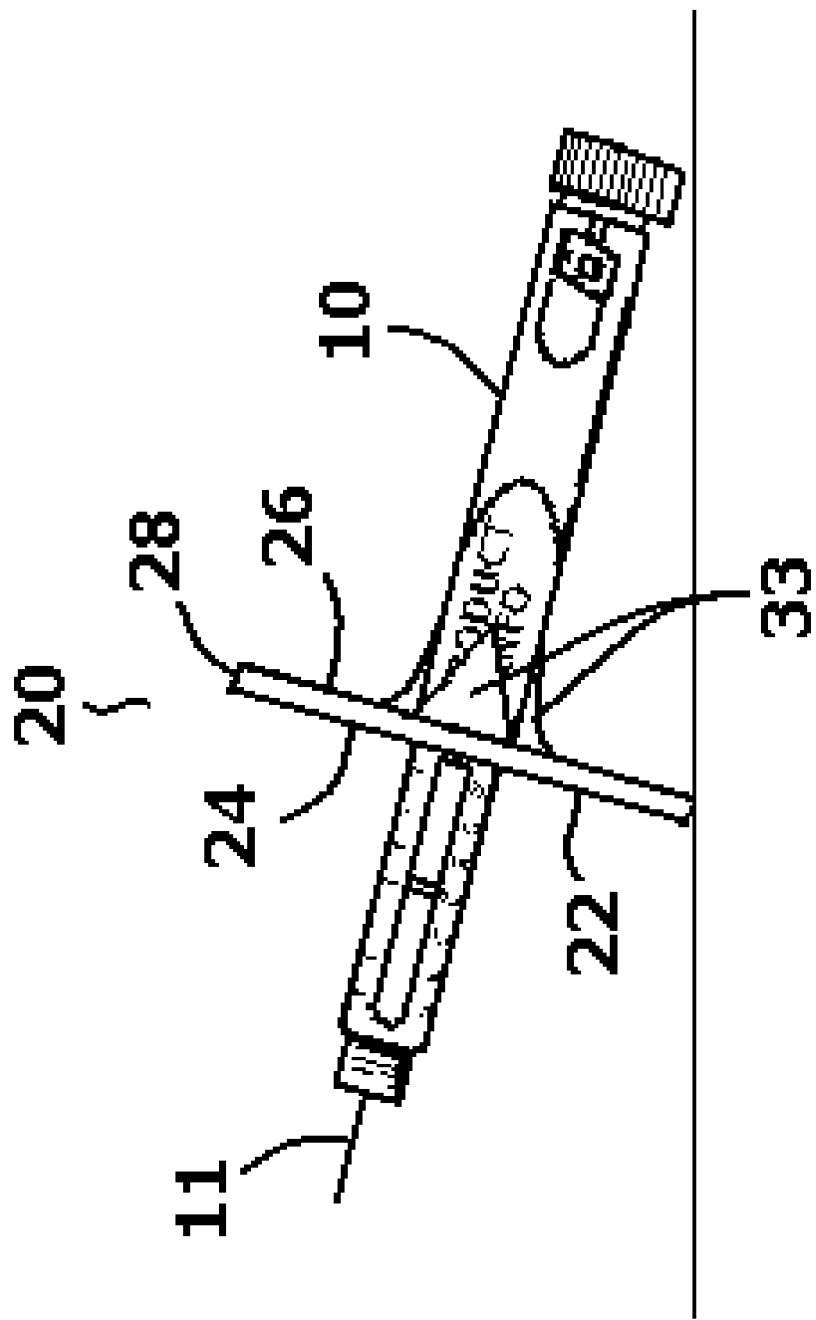
FIG. 3 shows a side view of the labeling system with the insulin pen.

Referring to FIG. 2 in conjunction with FIG. 3, an exemplary embodiment of the labeling system 20 is shown in conjunction with a prior art medication dispenser. In the illustrated case, the medication dispenser is a prior art insulin pen 10, such as that previously shown in FIG. 1. As can be seen, the labeling system 20 includes a panel 22. The panel 22 is planar in shape, having a top first surface 24 and an opposite bottom second surface 26 that share a common periphery. The periphery presents one or more side surfaces 28. The periphery of the panel 22 can be round. However, the periphery of the panel 22 is preferably shaped as a polygon to prevent rolling when placed on a surface. The number of side surfaces 28 in the polygon is preferably equal to the number of dose labels 30 to be used on the medication dispenser.

In the illustrated embodiment, the medicated dispenser is an insulin pen 10. Insulin pens are typically used four times a day. They are typically used at each meal and prior to bed. In a hospital, each dosage prescribed is provided with a label 30. As such, using the same example, the insulin pen 10 typically would be provided with four labels 30 at the beginning of a day. The four labels 30 contain barcodes or other scanning indicia that are used to track the administration of the insulin to a patient over the course of the day.

In the shown embodiment, it can be seen that the exemplary four labels 30 are attached to the first surface 24 of the panel 22. The four labels 30 align with the four side surfaces 28 of the panel 22. In this manner, any healthcare provider can simply look at the shape of the panel 22 and instantly determine that the medication associated with the panel 22 is to be administered four times daily. As an alternate example, it will be understood that an eight-sided panel can be used to hold eight labels for medication that should be administered eight times daily. Accordingly, the peripheral polygonal shape of the panel 22 is a visual indicator that corresponds to the dosage schedule. The shape of the panel 22, therefore, provides an instant visual indication as to the dosage schedule of the medication identified by the labels 30 on the panel 22.

In the center of the panel 22 is a cut opening 32. The cut opening 32 produces a series of flexible flaps 33 that face the center of the panel 22. The insulin pen 10 can be inserted through the cut opening 32. The insulin pen 10 bends the flaps 33 as the insulin pen 10 is inserted into the cut opening 32. The bent flaps 33 are biased towards the sides of the insulin pen 10 and press against the insulin pen 10. This causes the panel 22 to engage the insulin pen 10 with a strong and secure friction fit.

Once the insulin pen 10 is engaged with the flaps 33 at the cut opening 32, the panel 22 becomes a flange that radially extends away from the insulin pen 10. The flaps 33 only cover a small portion of the insulin pen 10. As such, the important elements on the exterior of the insulin pen 10 remain observable. Likewise, the functional elements on the exterior of the insulin pen 10 remain unobstructed.

Referring to FIG. 3, it can be seen that once the panel 22 is applied to the insulin pen 10, the presence of the panel 22 creates a radial flange that elevates the needle end 11 of the insulin pen 10. This prevents the needle end 11 of the insulin pen 10 from contacting any surface when it is placed to rest. This helps prevent the needle end 11 of the insulin pen 10 from becoming contaminated while waiting to be used. The inclined insulin pen 10 is also much easier to grasp and lift from an instrument tray or other flat surface. Lastly, the inclination of the panel 22 makes the labels 30 on the panel 22 easy to observe and scan.

The panel 22 is planar and is disposable. As such, the panel 22 is made as inexpensively as possible. The panel 22 can be cut from paperboard. However, to prevent issues of contamination, it is preferred that the panel 22 be made of synthetic, non-organic materials, such as a plastic or foam board. Foam board, which is a polystyrene foam sandwiched between smooth waxed sheets, does not readily harbor bacteria. Furthermore, foam board is rigid yet subtle enough to enable the cut opening 32 to bend and expand around the insulin pen 10 and engage the insulin pen 10 with a friction fit.

Figure 4:
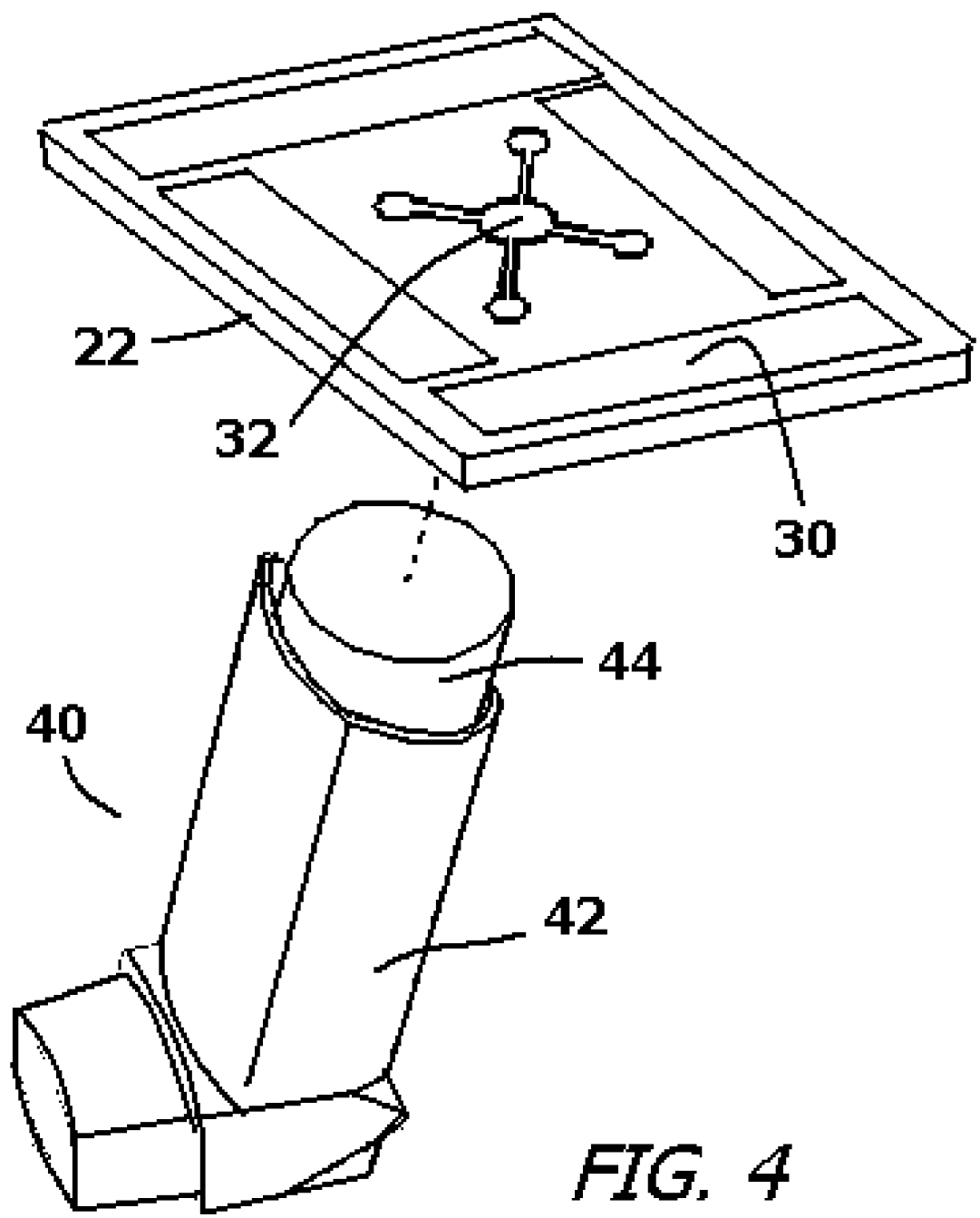
FIG. 4 shows an alternate embodiment where the labeling system engages an alternate medication dispenser.

Referring to FIG. 4, it will be understood that the panel 22 can be made in many different sizes and can be applied to many different medication dispensers. In the embodiment of FIG. 4, a medication dispenser is provided in the form of a pressurized inhaler 40. The inhaler 40 has a tubular shaft 42 that surrounds a pressurized container 44. The cut opening 32 in the center of the panel 22 is sized to pass around the tubular shaft 42. Once placed around the inhaler 40, the panel 22 radially extends from the tubular shaft 42. The panel 22 provides much more room for labels 30 than would otherwise be available on the inhaler 40.

It will be understood that the present invention can be applied to any medication dispenser assembly or storage container capable of passing into the cut opening 32 of the panel 22 and engaging the panel 22 with a friction fit. Medication dispenser assemblies and storage containers include, but are not limited to, syringes, inhalers, vials, pill containers, bottles and test tubes.

Figure 5:
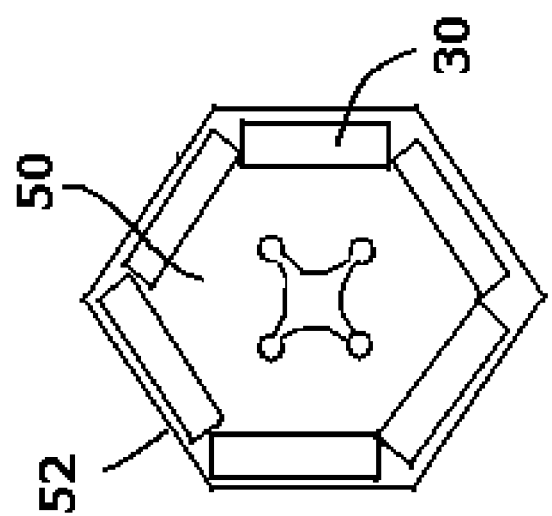
FIG. 5 shows an alternate embodiment of the labeling system having a panel with a polygonal shape.

In the embodiments shown in FIG. 1 through FIG. 4, the panel 22 is has a periphery shaped as a rhombus with four side surfaces 28 that is used to hold four labels 30. Referring to FIG. 5, it will be understood that the present invention labeling system 20 can utilize a panel 50 having a peripheral shape of any polygon. Although not required, the number of side edges 52 on the panel 50 corresponds to the number of labels 30 being applied. Of course, it is recognized that the more side edges 52 that are provided to the panel 50, the less room exists along the sides to place a label 30. The panel 50 can be made with a larger area. However, at some point, the panels 50 may lack the area needed to support the labels 30.

Figure 6:
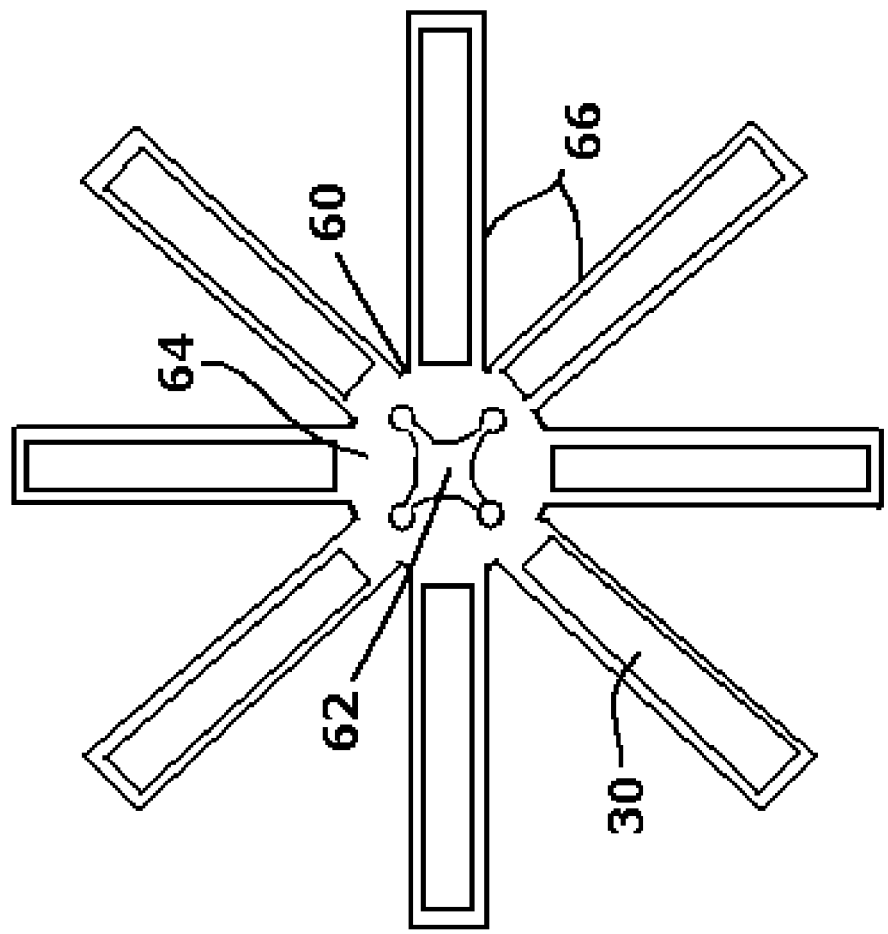
FIG. 6 shows an alternate embodiment of the labeling system having a panel with radial arms.

Referring to FIG. 6, a solution to this problem is provided. In this embodiment, a panel 60 is provided that is shaped as an asterisk. The panel 60 has a central hub 64 and arms 66 that radially extend from the central hub 64. A cut opening 62 is formed in the middle of the central hub 64. The cut opening 62 can engage a medication dispensing assembly or a medical storage container in the same manner as was described with the earlier embodiments.

A label 30 can be attached to each of the arms 66. In this manner, the labels 30 are arranged to radially extend away from the central hub 64. This optimizes the available space on the panel 60 and enables many labels 30 to be attached to a product without the system becoming overly burdensome.

Figure 7:
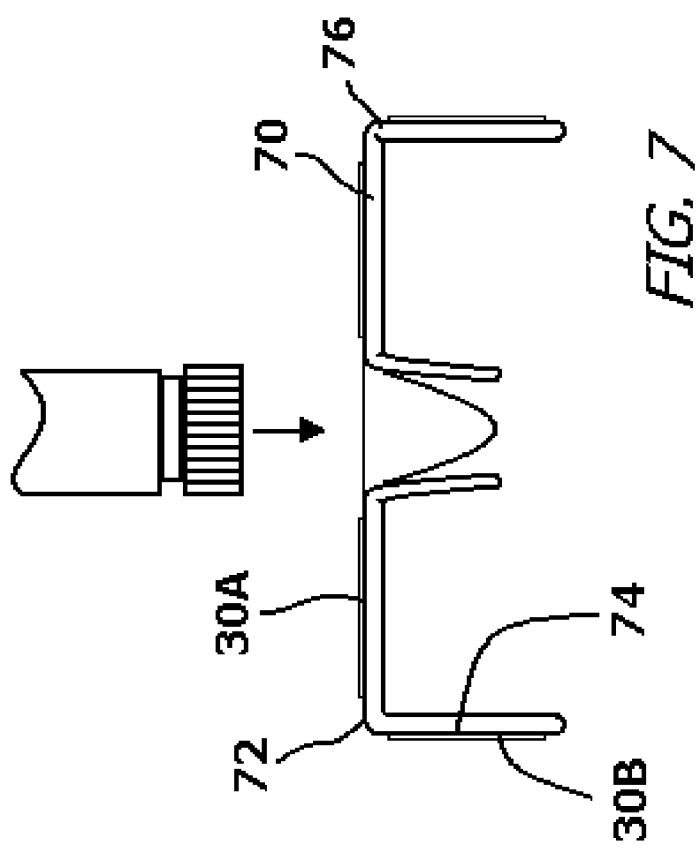
FIG. 7 shows an alternate embodiment of the labeling system having folded side walls.

In all previous embodiments, the panel used in the labeling system 10 has been planar. However, this need not be the case. Referring to FIG. 7, it can be seen that a panel 70 can be provided that has a flat top surface 72 and side surfaces 74 that are created by bends 76 in the panel 70. This orients the side surfaces 74 to be perpendicular to the primary plane of the top surface 72. The multiple side surfaces 74 created by the bends 76 provide more areas for the adhesion of labels 30A, 30B. Label 30A can be attached to the flat top surface 72. Additional labels 30B can be attached to the side surfaces 74.

The bends 76 in the panel 70 also make the overall device more stable, wherein the panel 70 can rest sideways on one of its side surfaces 74. The side surface 74 provides a wide, stable support base.

Figure 8:
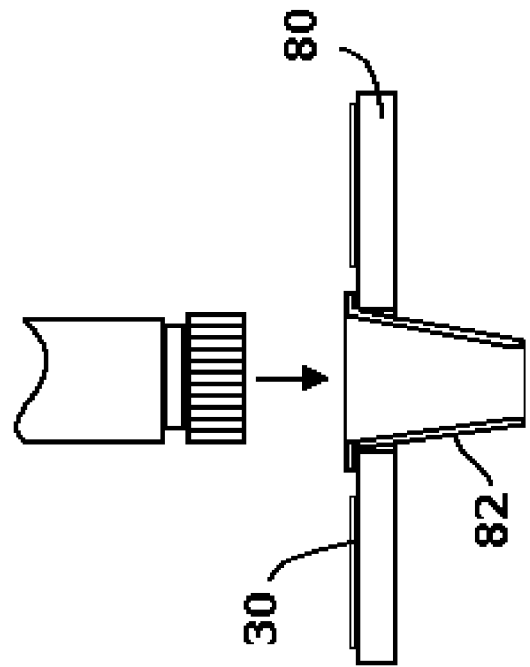
FIG. 8 shows an alternate embodiment of the labeling system having an elastomeric friction connector.

In all previous embodiments, the panel attaches to a medication dispenser using a cut opening. This need not be the case. Other friction connectors can be utilized. Referring to FIG. 8, such an alternate friction connector is presented. In FIG. 8, it can be seen that a hollow, frustum-shaped sleeve 82 is attached to the panel 80. The sleeve 82 is made from an elastic material or formed from an elastomeric polymer. As a medication dispenser 85 is inserted through the sleeve 82, the sleeve 82 expands and conforms to the shape of the medication dispenser 85. Friction holds the medication dispenser 85 in place and joins the panel 80 to the medication dispenser 85. The use of an elastic sleeve 82 is useful if the invention is being applied to any medication dispenser that has a bulky or complex exterior shape.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A labeling system for a medication dispenser, comprising:
    a panel having a first planar surface with a geometric center, wherein said first planar surface extends to a periphery having a polygonal shape;
    side walls extending at a perpendicular from said first planar surface along said periphery, wherein said side walls are formed by bends in said panel;
    an opening formed in said panel proximate said geometric center, wherein said opening is sized to receive said medication dispenser therein; and
    labels adhered to said first planar surface.

2. The system according to claim 1, wherein said polygonal shape provides said periphery of said panel with a first number of flat side surfaces and said labels adhered to said first planar surface correspond in number to said first number of flat side surfaces.

3. The system according to claim 1, wherein said opening in said panel forms flaps that can be displaced by said medication dispenser when said medication dispenser is within said opening.

4. The system according to claim 1, wherein said polygonal shape includes a plurality of panel arms that radially extend from a central panel hub.

5. The system according to claim 4, wherein said labels are applied to said panel arms.

6. A labeling system for a medication dispenser, comprising:
    a panel having a first surface with a geometric center, wherein said first surface extends to a shaped periphery;
    side walls that extend at a perpendicular from said first surface along said shaped periphery, wherein said side walls are formed by bends in said panel;
    an opening formed in said panel proximate said geometric center;
    a friction connector at said opening for engaging said medication dispenser when said medication dispenser is advanced into said opening; and
    labels adhered to said first surface.

7. The system according to claim 6, wherein said labels adhered to said first surface correspond in number to said side walls.

8. The system according to claim 6, wherein said friction connector includes flaps around said opening that are displaced by said medication dispenser when said medication dispenser is within said opening.

9. The system according to claim 6, wherein said friction connector includes an elastomeric tubular structure that passes around said medication dispenser when said medication dispenser is advanced within said opening.

10. The system according to claim 6, wherein said labels are applied to said side walls.

11. A system for labeling a medication dispenser, comprising:
    a medication dispenser;
    a label support panel having a first surface with a geometric center, wherein said first surface extends to a shaped periphery;
    side walls that extend from said first surface along said shaped periphery, wherein said side walls are formed by bends in said label support panel;
    an opening formed in said label support panel proximate said geometric center through which said medication dispenser extends, wherein said label support panel engages said medication dispenser with a friction connection;
    a friction connector at said opening for engaging said medication dispenser when said medication dispenser is advanced into said opening; and
    labels adhered to said first surface.

12. The system according to claim 11, wherein said shaped periphery of said panel has a first number of flat side surfaces and said labels adhered to said first surface correspond in number to said first number of flat side surfaces.

13. The system according to claim 11, wherein said friction connector includes flaps around said opening that are displaced by said medication dispenser when said medication dispenser is within said opening.

14. The system according to claim 11, wherein said friction connector includes an elastomeric structure that passes around said medication dispenser when said medication dispense is advanced within said opening.

* * * * *